United States Patent [19]

Cello et al.

[11] Patent Number: 4,459,355

[45] Date of Patent: Jul. 10, 1984

[54] METHOD FOR TRANSFORMING PLANT CELLS

[75] Inventors: Linda M. Cello, Highland Mills; William L. Olsen, Warwick, both of N.Y.

[73] Assignee: International Paper Company, New York, N.Y.

[21] Appl. No.: 397,612

[22] Filed: Jul. 12, 1982

[51] Int. Cl.$^3$ .................. C12N 15/00; C12N 5/00
[52] U.S. Cl. ........................... 435/172.3; 435/240; 935/30; 935/64; 935/35; 935/55; 935/67
[58] Field of Search .................. 435/192, 240

[56] References Cited

U.S. PATENT DOCUMENTS 4,237,224 12/1980 Cohen et al. ................. 435/68
4,259,444 3/1981 Chakrabarty ................. 435/172

FOREIGN PATENT DOCUMENTS

WO79/01169 6/1979 PCT Int'l Appl. .

OTHER PUBLICATIONS

Hooykaas et al., Genetic Engineering by Sellow et al., Plenum Press, pp. 151-179, (1979).
Davey et al., "Transformation of Petunia Protoplasts by Isolated *Agrobacterium* Plasmids", *Plant Science Letters* 18, 307-313, (1980).
Drummond, "Crown Gall Disease", *Nature* 281, 343-347, (1979).
Einset et al., "Regeneration of Tobacco Plants from Crown Gall Tumors", in Vitro 15, 703-708, (1979).
Firmin et al., "Agropine-A Major New Plasmid Determined Metabolite in Crown Gall Tumors", *Nature* 276, 842-844, (1978).
Hildebrand, "A Micrurgical Study of Crown Gall Infection in Tomato", *Journal of Agricultural Res.* 65, 45-58, (1942).
Krens et al., "In Vitro Transformation of Plant Protoplasts with Ti-Plasmid DNA", *Nature* 296, 72-74, (1982).
Matthysse et al., "Elaboration of Cellulose Fibrils by *Agrobacterium tumefaciens* During Attachment to Carrot Cells", *Journal of Bacteriology* 145, 583-595, (1981).
Matthysse et al., "Binding of *Agrobacterium tumefaciens* to Carrot Protoplasts", *Physiological Plant Pathology* 20, 27-33, (1982).
Petit et al., "Substrate Induction of Conjugative Activity of *Agrobacterium Tumefaciens* Ti Plasmids", *Nature* 271, 570-571, (1978).
Yang et al., "Foreign DNA Sequences in Crown Gall Teratomas and their Fate during the Loss of the Tumorous Traits", *Molec. Gen. Genet.* 177, 707-714, (1980).

*Primary Examiner*—Alvin E. Tanenholtz
*Attorney, Agent, or Firm*—Richard J. Ancel

[57] ABSTRACT

A method for transforming a plant cell in vitro with a Ti plasmid. The method involves inoculating the plant cell with a strain of *Agrobacterium tumefaciens*, containing the Ti plasmid, in the presence of an opine metabolite, that is normally synthesized only by a plant cell which has already been transformed by the Ti plasmid, or in the presence of the precursors of the opine metabolite. However, the opine metabolite or its precursors, which are used, must also be able to induce conjugative activity of the Ti plasmid.

8 Claims, No Drawings

METHOD FOR TRANSFORMING PLANT CELLS

BACKGROUND OF THE INVENTION

This invention relates to a novel method for transforming plant cells in vitro with *Agrobacterium tumefaciens*.

Certain strains of *A. tumefaciens* are responsible for crown gall disease in dicotyledons and gymnosperms. The disease is caused by a bacterium of such a strain attaching itself to the surface of a cell of a plant, at a wound site on the plant, and then transferring into the plant cell a large tumor-inducing (Ti) plasmid. The infected plant cell is thereby transformed into a gall (tumor) cell.

In crown gall disease, only portions of the Ti plasmid, transferred into a plant cell by an oncogenic strain of *A. tumefaciens*, are actually inserted into the plant cell's nuclear DNA. The inserted portions of the Ti plasmid (T-DNA), which can remain indefinitely in the plant cell's DNA, code for several functions which are expressed by the transformed plant cell. Such functions include tumorigenesis and the synthesis of abnormal opine metabolites that are specific to the Ti plasmid, transferred into the plant cell.

In recent years, the study of crown gall disease has become of importance because it may shed light on ways of controlling carcinogenesis and on ways of controlling gene expression in higher plants. In this regard, there has been particular interest in the possibility of using a Ti plasmid from an oncogenic strain of *A. tumefaciens* as a cloning vehicle or genetic vector for transforming higher plants. See Drummond, "Crown Gall Disease", *Nature* 281, 343–347 (1979).

However, only two ways have heretofore been known for transforming a plant cell with a Ti plasmid:

(1) By infecting an entire plant with crown gall disease (by applying oncogenic *A. tumefaciens* cells to a fresh wound on the plant) and then removing crown gall cells which develop on the plant; or (2) By isolating Ti plasmids and protoplasts of plant cells, transferring in vitro the Ti plasmids into the plant cell protoplasts, and then culturing the transformed protoplasts to produce plant cells.

Both ways have been relatively time-consuming and burdensome to carry out. As a result, it has been difficult to conduct experiments on plant cells with crown gall disease in the laboratory.

A more direct and simpler way of transforming a plant cell with a Ti plasmid has therefore been sought which would not require either the infection of an entire plant or the isolation of both the Ti plasmid and a protoplast of the plant cell.

SUMMARY OF THE INVENTION

In accordance with this invention, a method is provided for transforming a plant cell in vitro with a Ti plasmid. The method comprises:

inoculating the plant cell with a strain of *A. tumefaciens*, containing the Ti plasmid, in the presence of an opine metabolite, that is normally synthesized only by a plant cell which has already been transformed by the Ti plasmid, or in the presence of the precursors of the opine metabolite; said opine metabolite or its precursors being capable of including conjugative activity of said Ti plasmid.

By this method, a plant cell can be directly transformed with a Ti plasmid, without the need for infecting an entire plant and without the need for isolating a protoplast of the plant cell and isolating the Ti plasmid.

DETAILED DESCRIPTION OF THE INVENTION

In accordance with the method of this invention, a plant cell is transformed in vitro with a Ti plasmid by inoculating the cell with a strain of *A. tumefaciens* which contains the Ti plasmid. This method is carried out in the presence of an opine metabolite, which only a transformed plant cell normally synthesizes, or preferably, in the presence of the precursors of the opine metabolite.

In carrying out the method of this invention, the use of a specific type of Ti plasmid is not critical. In this regard, one can use any of the three known types of Ti plasmids: (1) an octopine Ti plasmid which normally triggers the synthesis, in a transformed plant cell, of octopine together with octopinic acid, lysopine, histopine and, with some plasmids, agropine; (2) a nopaline Ti plasmid which normally triggers the synthesis, in a transformed plant cell, of nopaline together with nopalinic acid; or (3) an agropine Ti plasmid which normally triggers agropine synthesis in a transformed plant cell. However, in carrying out this method with a cell of a specific plant, the Ti plasmid, utilized, should be one which can cause crown gall disease in that plant.

Also in this method, the use of a specific strain of *A. tumefaciens* is not critical. In this regard, any oncogenic strain of *A. tumefaciens* can be used which can transfer its own Ti plasmid to the plant cell, to be transformed. If desired, a normally non-oncogenic strain of *A. tumefaciens* can be used which has been rendered oncogenic by receiving a Ti plasmid from another strain of *A. tumefaciens*. For example, a strain of *A. tumefaciens* can be used that obtained a Ti plasmid by conjugation in accordance with Petit et al, "Substrate Induction of Conjugative Activity of *Agrobacterium tumefaciens* Ti Plasmids", *Nature* 271, 570–571 (1978).

Also in this method, the use of a cell from a specific type of plant is not critical. In this regard, a cell from any plant, into which a Ti plasmid can be transferred by a strain of *A. tumefaciens*, can be utilized. For example, the plant cell can come from any dicotyledon, such as tomato and tobacco, and from any gymnosperm, such as loblolly pine, cedar and Douglas fir.

In carrying out the method of this invention with a specific Ti plasmid, one can use any opine metabolite or its precursors, provided:

(1) a plant cell, transformed with the specific Ti plasmid, normally synthesizes the opine metabolite; and (2) the opine metabolite or its precursors can induce conjugative activity of the specific Ti plasmid, i.e., cause the transfer of the Ti plasmid from one strain of *A. tumefaciens* to another by a process as described by Petit et al, "Substrate Induction of Conjugative Activity of *Agrobacterium tumefaciens* Ti Plasmids", *Nature* 271, 570–571 (1978).

For example, this method can be carried out by inoculating a plant cell with a strain of *A. tumefaciens*, having an octopine Ti plasmid, in the presence of: octopine or its precursors, i.e., arginine and pyruvate; opine metabolites which are synthesized concomitantly with octopine, i.e., lysopine and octopinic acid; the precursors of lysopine, i.e., lysine and pyruvate; or the precursors of octopinic acid, i.e., ornithine and pyruvate; and preferably in the presence of octopine or its precursors, especially in the presence of its precursors.

If desired, the Ti plasmid, used in the method of this invention, can be a Ti plasmid into which a DNA sequence has been inserted. Such a DNA sequence can be derived from the genome of a bacteria or a plant or can be synthetic. The DNA sequence can contain a gene or a DNA fragment of a gene which codes for a particular protein which confers, for example, resistance to a herbicide or to a disease (e.g., resistance to the disease in tomatoes of fusarium wilt). The DNA sequence, inserted into the Ti plasmid, can also code for one or more regulatory elements (e.g., a translational start signal) which control expression of the particular protein in a cell.

A DNA sequence can be inserted into the Ti plasmid by, for example, inserting the DNA sequence into the T-DNA of the Ti plasmid so that the DNA sequence is in the same reading frame as the T-DNA. The general procedure of Cohen et al U.S. Pat. No. 4,237,224 can be used for inserting the DNA sequence into the T-DNA. Then, the resulting hybrid Ti plasmid can be used as a genetic vector to insert both its T-DNA and the inserted DNA sequence into the DNA of a plant cell, whereby the plant cell will express both the T-DNA and the gene or its DNA fragment from the inserted DNA sequence.

Such insertion of a DNA sequence into the Ti plasmid should not interfere significantly with the ability of the resulting hybrid Ti plasmid to be transferred in vitro from a cell of *A. tumefaciens* into a plant cell and to have its T-DNA inserted into the DNA of the plant cell in accordance with this invention. Such a hybrid Ti plasmid will, however, be adapted also to insert the gene or its DNA fragment from the inserted DNA sequence into the DNA of the plant cell. Hence, the term "Ti plasmid" herein encompasses both hybird and wild-type Ti plasmids that have the DNA sequences which code for the essential functions required to transfer a Ti plasmid in vitro from a cell of *A. tumefaciens* into a plant cell and then to insert the T-DNA of the Ti plasmid into the plant cell DNA by the method of this invention.

A plant cell, transformed with a Ti plasmid in accordance with this invention, can be used in a conventional manner to regenerate a plant that expresses one or more functions, for which the Ti plasmid codes. For example, a plant can be regenerated from a plant cell, that has been transformed by the method of this invention, using the procedure generally described by Einset et al, "Regeneration of Tobacco Plants from Crown Gall Tumors", In Vitro 15, 703–708 (1979).

The examples, which follow, further illustrate this invention. The following bacterial growth medium was utilized in the examples: M-9 Medium 10 ml of aqueous 0.1M MgSO$_4$, 10 ml of aqueous 20% (wt/vol) glucose, 10 ml of aqueous 20% (wt/vol) casamino acids and 1 liter of the following aqueous (autoclaved and cooled) solution:

|  | g/l |
|---|---|
| Na$_2$HPO$_4$ | 6.0 |
| KH$_2$PO$_4$ | 3.0 |
| NaCl | 0.5 |
| NH$_4$Cl | 1.0 |

The plant cell growth medium comprised:

20 g/l sucrose and 9 g/l agar, added to the following aqueous, Gresshoff and Doy No. 1 solution (ph adjusted to 5.6±0.1):

|  | mg/l |
|---|---|
| KNO$_3$ | 1,000 |
| MgSO$_4$.7H$_2$O | 250 |
| (NH$_4$)$_2$SO$_4$ | 200 |
| CaCl$_2$.2H$_2$O | 150 |
| KCl | 300 |
| NaH$_2$PO$_4$.H$_2$O | 90 |
| Na$_2$HPO$_4$ | 30 |
| MnSO$_4$.H$_2$O | 10 |
| ZnSO$_4$.7H$_2$O | 3 |
| H$_3$BO$_3$ | 3 |
| KI | 0.75 |
| CuSO$_4$.5H$_2$O | 0.25 |
| Na$_2$MoO$_4$.2H$_2$O | 0.25 |
| CoCl$_2$.6H$_2$O | 0.25 |
| FeSO$_4$.7H$_2$O | 27.8 |
| Na$_2$EDTA | 37.3 |
| Myo-inositol | 10 |
| Thiamine.HCl | 1 |
| Nicotinic Acid | 0.1 |
| Pyridoxine HCl | 0.1 |

The inoculation medium was the plant cell growth medium, without the added agar but with the added sucrose.

In the examples, *A. tumefaciens* ATCC No. 15955 was utilized. This strain was obtained from the American Type Culture Collection, Rockville, Md. *A. tumefaciens* 15955 carries the Ti plasmid pTi 15955, which causes the cell of an infected plant, transformed by the plasmid, to synthesize octopine. This strain of *A. tumefaciens* has been shown to produce galls on a wide range of dicotyledonous plants.

EXAMPLES

The A. Tumefaciens Culture

Cultures of *A. tumefaciens* 15955 were maintained on nutrient agar at 25° C. Cultures were grown in M-9 medium and incubated overnight at 25° C. on a gyratory shaker (Model G-2, New Brunswick Scientific, Co., Inc., Edison, N.J.) at 200 rpm.

The Plant Cells

Tomato callus cells were obtained from tomato seeds (Burpee, Big Boy variety) by surface sterilizing the seeds with full strength Clorox bleach, rinsing the seeds with sterile water, and germinating the seeds on sterile filter paper. Germinated seeds (about 1 week old) were again surface sterilized with 10% Clorox bleach to eliminate any fungel and/or bacterial contamination from within the seeds. The opened seed coats were removed, and the seedlings were chopped-up with a sterile scalpel and placed on the plant cell growth medium, supplemented with 0.2 μg/ml 1-naphthalene-acetic acid (NAA).

The cells of the tomato callus on the plant cell growth medium were incubated at 25° C. under constant light and subcultured every 3 to 4 weeks onto fresh plant cell growth medium supplemented with 0.2 μg/ml NAA.

In vitro Inoculation

The Tomato callus was chopped-up with a sterile scalpel, and pieces of the callus were aseptically placed in 20 ml of:

A. the liquid inoculation medium (containing sucrose but no agar), supplemented with 0.2 µg/ml NAA [Example A];
B. the liquid inoculation medium, supplemented with 0.2 µg/ml NAA, 10 mM arginine and 10 mM pyruvate [Example B];
C. the liquid inoculation medium, supplemented with 0.2 µg/ml NAA and 10 mM octopine [Example C]; and
D. the liquid inoculation medium, supplemented with 0.2 µg/ml NAA and 25 ml plant wound filtrate (obtained by nicking the stems of tomato seedlings, excising wound sites after 48 hours, grinding the wound site tissue with mortar and pestle, and filter sterilizing the ground-up tissue through a nitrocellulose filter of 0.22 micron pore size, with the aid of suction, to remove any bacteria from the filtrate) [Example D].

The cells of the pieces of callus in each example were then inoculated with approximately $10^6$ A. tumefaciens 15955 cells/ml from an overnight M-9 medium culture. The inoculated callus cell cultures were incubated at 25° C. on a gyratory shaker at 200 rpm.

Culturing Inoculated Plant Cells

Pieces of callus cells were removed from the liquid inoculation medium in each example prior to inoculation with A. tumefaciens 15995 [the control] and at various times, up to 48 hours, after inoculation [Examples A to D]. The removed pieces of callus cells were washed thoroughly with aqueous solutions containing 200 µg/ml of each of the antibiotics, vancomycin, ampicillin and streptomycin (obtained from Sigma Biochemicals, St. Louis, Missouri) to inhibit growth of any bacteria remaining on callus cell surfaces. The pieces of callus cells were then placed on the plant cell growth medium, containing 0.2 µg/ml NAA and the same antibiotics.

The pieces of callus cells were, thereafter, subcultured every 3 to 4 weeks onto fresh plant cell growth medium, supplemented with 0.2 µg/ml NAA (without antibiotics). After 3 subculturings, the pieces of callus cells were placed on the plant cell growth medium (without NAA) and incubated at 25° C. under constant light.

The results of the foregoing Examples A, B, C and D are summarized in the Table, below. The uninoculated pieces of callus cells [the control], the pieces of callus cells inoculated in the plant cell growth medium plus NAA [Example A] and the pieces of callus cells inoculated in the plant cell growth medium plus NAA and plant wound filtrate [Example D] died soon after being placed on the plant cell growth medium (without NAA). However, about 35% of the pieces of callus cells inoculated in plant cell growth medium plus NAA and arginine and pyruvate [Example B] and about 7% of the pieces of callus cells inoculated in plant cell growth medium plus NAA and octopine [Example C] remained viable and grew slowly after being subcultured onto the plant cell growth medium (without NAA). This shows that only in Examples B and C, where inoculation was carried out in the presence of arginine and pyruvate or octopine, were the callus cells transformed by the Ti plasmid of the A. tumefaciens 15955 cells.

The percentage of pieces of callus cells, which were transformed in Examples B and C, did not increase significantly after the first 2 hours after inoculation with A. tumefaciens 15955.

The pieces of callus cells, which had been inoculated in Examples B and C and which remained viable and grew slowly on the plant cell growth medium, even after being subcultured 8 to 10 times, were assayed for the presence of octopine synthetase after 16 weeks on the plant cell growth medium.

Octopine synthetase activity was assayed by incubating each sample of callus cells for 48 hours in 2 ml of the inoculation medium, supplemented with 2.0 µg/ml NAA and 100 mM arginine. After incubation, the cells were thoroughly washed three times with distilled water and ground in 1.0 ml distilled water, using a 10 ml glass tissue homogenizer and a teflon pestle. The supernatant was decanted into a 1.5 ml polypropylene micro-Eppendorf centrifuge tube and centrifuged for 2 minutes at full speed in an Eppendorf 5412 centrifuge to remove cellular debris. Aliquots (10 to 20 µl) of the supernatant were spotted onto Whatman 3 MM paper. Where low levels of octopine synthetase activity were suspected, 100 to 200 µl supernatant was concentrated to dryness under nitrogen and resuspended in 10 µl of distilled water before spotting. Arginine (4 mg/ml) and octopine (6 mg/ml) were spotted as controls (2 µl). Crystals of methyl green were dissolved in ethanol and used as a tracking dye. Electrophoresis was performed in formic acid:glacial acetic acid:distilled water (5:15:80 parts by volume) for 30 minutes at 360 V (approximately 26 mA), on a Gelman paper electrophoresis unit. The electrophorogram was dried completely before staining with a freshly prepared solution of 2 mg phenanthrenequinone (Sigma Biochemicals, St. Louis, Mo.) dissolved in 10 ml absolute ethanol, filtered through Whatman No. 1 filter paper and mixed with 1 g NaOH dissolved in 10 ml of 60% ethanol. After drying, the electrophorogram was observed under long wave UV light and photographed with an industrial Polaroid camera, MP-8, using No. 52 film and a red (No. 54) filter. Octopine and arginine (as a standard) appeared as bright green, fluorescent spots.

Octopine was detected in pieces of callus cells, inoculated in the presence of arginine and pyruvate [Example B], and in pieces of callus cells, inoculated in the presence of octopine [Example C]. This confirmed the fact that the T-DNA of the Ti plasmid of the A. tumefaciens 15955 cells had become integrated into the genome of the callus cells in both Examples B and C.

TABLE

| Example | Additive to Inocul. Medium (Besides NAA) | Number of Callus Pieces Placed On Plant Cell Growth Medium After Inocul. | Number of Viable Callus Pieces After 16 Weeks On Plant Cell Growth Medium | Octopine Synthet. Activity |
|---|---|---|---|---|
| Control | None | 55* | 0 | — |
| A | None | 65 | 0 | — |
| B | Arginine + Pyruvate | 85 | 27 | + |
| C | Octopine | 85 | 5 | + |
| D | Plant Wound Filtrate | 25 | 0 | — |

*The 55 callus pieces were not inoculated.

It is thought that the invention and many of its attendant advantages will be understood from the foregoing description, and it will be apparent that various changes can be made in the steps of the method described and in the materials used in the method without departing from the spirit and scope of the invention or sacrificing all of its material advantages, the method hereinbefore described being merely a preferred embodiment thereof.

We claim:

1. A method for transforming a crown gall disease susceptible plant cell in vitro with a Ti plasmid that can cause crown gall disease in said plant cell, comprising: inoculating the plant cell in vitro with a strain of *Agrobacterium tumefaciens*, containing the Ti plasmid, in the presence of an opine metabolite, that is normally synthesized only by a plant cell which has already been transformed by the Ti plasmid, or in the presence of the precursors of the opine metabolite; said opine metabolite or the precursors being capable of inducing conjugative activity of said Ti plasmid.

2. The method of claim 1 wherein the Ti plasmid is an octopine Ti plasmid.

3. The method of claim 2 wherein the plant cell is inoculated in the presence of octopine or in the presence of arginine and pyruvate.

4. The method of claim 3 wherein the plant cell is inoculated in the presence of arginine and pyruvate.

5. The method of claim 1 wherein the crown gall disease susceptible plant cell is selected from the group consisting of dicotyledons and gymnosperms.

6. The method of claim 5 wherein the dicotyledon is selected from the group consisting of tomatoes and tobacco.

7. The method of claim 5 wherein the gymnosperm is selected from the group consisting of loblolly pine, cedar, and Douglas fir.

8. The method of claim 1 wherein the *Agrobacterium tumefaciens* strain is selected from the group consisting of oncogenic strains of *A. tumefaciens* and non-oncogenic strains of *A. tumefaciens* which have been rendered oncogenic by the insertion therein of a Ti plasmid from an oncogenic strain of *A. tumefaciens*.

* * * * *